Figure 2:
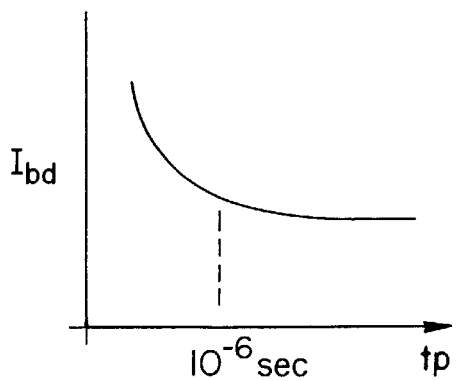
Figure 3:
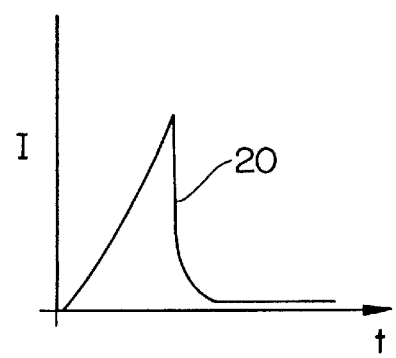

United States Patent [19]
Smith

[11] Patent Number: 6,028,723
[45] Date of Patent: Feb. 22, 2000

[54] PROTECTING EYES AND INSTRUMENTS FROM SHORT PULSE LASER RADIATION

[76] Inventor: David C. Smith, 44 Candlelight Dr., Glastonbury, Conn. 06033

[21] Appl. No.: 09/176,986

[22] Filed: Oct. 22, 1998

Related U.S. Application Data

[63] Continuation-in-part of application No. 08/822,841, Mar. 24, 1997, abandoned.

[51] Int. Cl.⁷ .................................. G02B 5/22; G02F 1/29
[52] U.S. Cl. .......................... 359/885; 359/299; 359/634; 351/44; 250/216
[58] Field of Search ...................................... 359/243, 297, 359/350–366, 589–590, 601–614, 507, 480, 885; 351/16, 2–163, 44, 156, 213; 250/216, 347; 372/35, 103

[56] References Cited

U.S. PATENT DOCUMENTS

| | | | |
|---|---|---|---|
| 4,890,075 | 12/1989 | Pohlmann et al. | 330/4.3 |
| 5,280,169 | 1/1994 | Honey et al. | 250/216 |
| 5,283,697 | 2/1994 | Tutt et al. | 359/885 |
| 5,491,579 | 2/1996 | Justus et al. | 359/601 |
| 5,739,947 | 4/1998 | Wood et al. | 359/885 |
| 5,828,437 | 10/1998 | Habart et al. | 359/480 |
| 5,831,769 | 11/1998 | Smith | 359/634 |

OTHER PUBLICATIONS

David C. Smith, Gas breakdown initialed by laser radiation interaction with aerosols and solid surfaces. Jounal of Applied Physics, vol. 48, Jun. 1977, pp 2217–2225.

*Primary Examiner*—Thong Nguyen
*Attorney, Agent, or Firm*—M. P. Williams

[57] ABSTRACT

A lens system for protecting high gain optical systems (eyes or equipment) from high intensity laser radiation includes a second mirror disposed on an exit lens, a first mirror formed by half silvering the inner surface of a focusing entry lens, and a medium such as sugar water containing aerosol particles of three-micron carbon, which induces ionization that will absorb the incoming laser radiation. One binocular embodiment uses the foregoing medium; a second binocular embodiment uses a solid lens material laden with aerosol particles.

29 Claims, 2 Drawing Sheets

PROTECTING EYES AND INSTRUMENTS FROM SHORT PULSE LASER RADIATION

CROSS REFERENCE TO RELATED APPLICATIONS

This application is a continuation-in-part of U.S. patent application Ser. No. 08/822,841 filed Mar. 24, 1997, now abandoned.

TECHNICAL FIELD this invention relates to particle induced gas breakdown to cause laser power absorption in a protective lens.

BACKGROUND ART

Although many nations of the world have joined in a treaty to preclude the use of lasers as anti-personnel weapons, some of the more radical nations in the world may yet decide to use laser radiation as a weapon against individuals. There are numerous laser-operated weapon guidance devices, including target designators in which the target, such as an aircraft, is "painted" with laser radiation, and a guidance system homes in on that radiation. In either of these cases, it is quite possible that humans will be subjected to laser radiation sufficient to damage the eye. Furthermore, the onset of the laser radiation may be very sudden, giving insufficient time to prepare for it. In order to quantify, to some extent, the effects of high intensity laser radiation on human eyes, some of the following analysis utilizes data related to rabbits and monkeys presented by Birngruber et al, "Femtosecond Laser-Tissue Interactions: Retinal Injury Studies", IEEE Journal of Quantum Electronics, Volume QE-23, No. 10, October 1987, pp. 1836–1844. It is believed that the eye has an optical gain of anywhere from 20,000 to 100,000; that is, the intensity of radiation entering through the iris is amplified 20,000 to 100,000 times as it is focused on the retinal spot at the back of the eye. The retinal spot is on the order of 50 microns in diameter, or smaller, and it is understood that laser intensity of wavelengths between 4 K Angstrom and 14 K Angstrom of on the order of 2,000 watts per square centimeter, or more, will burn the retinal spot; that is, will permanently damage the retina to preclude vision. The human eye has a protection reflex which operates in about one-quarter second. Either the eye will close or the head will turn away from the irritating radiation in about that length of time. Therefore, one could anticipate that a weapon intentionally designed to blind personnel would have a wavelength which the eye will not respond to (that is, not between 8 K Angstroms and 14 K Angstroms) or if having a visible wavelength, will have suitable power to do all the necessary damage in less than one-quarter second. FIG. 12 of Birngruber, et al describes the dependence, in rabbits and monkeys, of retinal injury threshold upon laser pulse duration. That data, however, relates to intensity of radiation at the retina; due to the high gain of the eye, the intensity of radiation outside the eye to achieve the data referred to in the figure is less by a factor of between 20,000 and 100,000. Therefore, radiation of on the order of, say, thirty milliwatts per square centimeter entering the iris, over a duration as small as one microsecond, is sufficient to reach the threshold of permanent damage at the retina. This compares with one milliwatt per square centimeter which is deemed unsafe; that is, it is painful but not inducing permanent damage (American Standard Institute ANSI Z136.1-1993).

It is understood that all eye protection known to the art simply utilizes attenuation, in many cases wavelength selective attenuation, to tend to protect eyes while still permitting the eye to see something of interest. In the case of laser radiation discussed hereinbefore, the degree of attenuation in the visible range would have to be sufficiently great so as to totally preclude any ordinary, ambient light reaching the eye in the absence of the radiation from a laser. Of course, totally filtering, by attenuation, radiation outside the visible range would still leave the eye subject to intentional destruction by lasers in the visible range.

The foregoing analysis is applicable to non-living optical systems which have extremely high gain within their optical receiving systems. This includes a variety of instruments, such as satellite surveillance systems. As used herein, the terms "high gain optics" and "high gain optical systems" include the human eye or eyes, and instruments which have significant optical gain and thereby may take advantage of the present invention.

Further, in the case of search or guidance instruments which are protected by narrow band filters having a center wavelength at the expected wavelength of a countermeasure of some sort, the countermeasure can switch wavelengths quite easily (such as by use of various isotopes of the lasing medium), thereby to mitigate the effectiveness of the filter. It is also known that a laser receptor protected by attenuators with narrow wavelength bands, in order to "see" in other portions of the visible spectrum, can be countermeasured easily, because all lasers can be shifted in wavelengths by large percents by various means such as isotopes of the lasing media, and therefore negate the attenuation protection.

In my prior U.S. Pat. No. 5,831,769, protection from laser pulses of greater than about one microsecond is provided.

Because thermal blooming requires a certain amount of time, the effective defocusing will occur only for laser radiation greater than about one microsecond duration, including continuous wave.

DISCLOSURE OF INVENTION

Objects of the present invention include protecting high gain optical systems from damage due to laser pulses having a duration between a femtosecond ($10^{-15}$) and a microsecond ($10^{-6}$) at wavelengths transmitted by the eye or other high gain optical systems of interest.

The present invention is predicated on my discovery of increasing the spatial energy density of laser radiation to a level at which it will vaporize an aerosol particle, the ionic vapor of which will assist in further ionization which will absorb all subsequent laser radiation, within limits.

According to the present invention, a lens system for protecting high gain optical systems from laser radiation pulses of about one microsecond duration and less includes an entry lens which focuses the incoming radiation, which may be either normal, visible or other desired light, or which may be harmful laser radiation, to a small spot, thereby to increase the spatial density of energy of incoming harmful laser radiation to a level at which it will vaporize an aerosol particle thereby to induce the absorption of the laser radiation, any unabsorbed light (including normal light) is passed through an exit lens to a high gain optical system, such as the eye or equipment. In some embodiments, an aerosol of three micron carbon particles in water is utilized as the ionizing medium; in another embodiment, an aerosol of carbon particles in carbonate or glass is utilized as the ionizing medium.

In one embodiment of the invention, a Cassigrain-like two mirror optical system with an entry lens which focuses the incoming radiation to a small spot which is just in front of a convex mirror which is the first mirror of an optical system, the second mirror of which is half-silvered surface on the inside of the entry lens, the reflections from which are collimated and passed through an exit lens. A second embodiment comprises a normal binocular system which focuses the radiation at a central point so as to vaporize an aerosol particle. A third embodiment includes a solid lens material, such as glass or carbonate, having entry and exit binocular lenses formed at the ends thereof, the solid being laden with aerosol particles.

Figure 1:
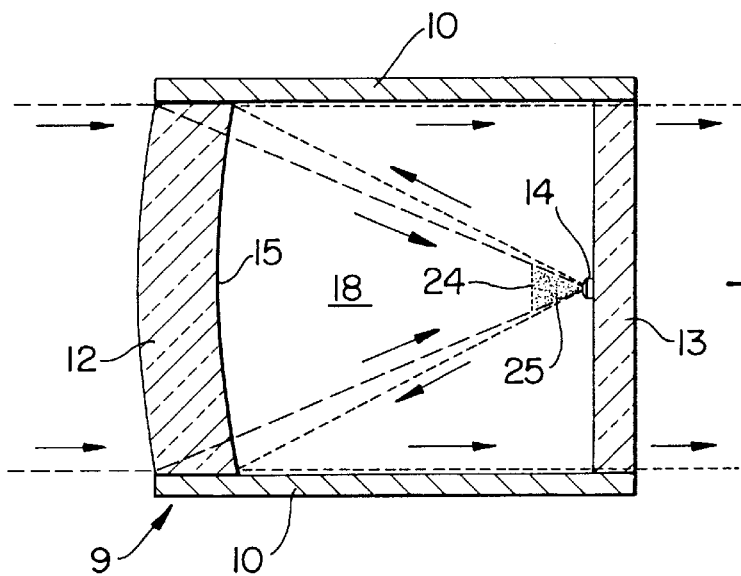

According further to the invention the aforementioned lens system may be used in series with a prior system having an index of refraction which varies spatially periodically along a dimension perpendicular to the collimated output of said lens system, which causes thermal distortion of the radiation of pulses having a microsecond duration and longer.

Other objects, features and advantages of the present invention will become more apparent in the light of the following detailed description of exemplary embodiments thereof, as illustrated in the accompanying drawing.

BRIEF DESCRIPTION OF THE DRAWINGS

FIG. 1 is a sectioned side elevation view of one embodiment of the present invention;

FIG. 2 is a plot of intensity of laser radiation required to cause a clean gas breakdown in air;

FIG. 3 is a plot of the intensity of radiation passing through an ionizable medium as a function of time after breakdown;

FIG. 4 is a simplified schematic block diagram of a system for protecting against short pulse, long pulse and continuous wave laser radiation;

FIG. 5 is a partial, simplified side elevation view of an eye and eyeglass employing the invention; and FIG. 6 is a sectioned, side elevation view of a second embodiment of the invention; and FIG. 7 is a sectioned, side elevation view of a third embodiment of the invention.

Best Mode for Carrying Out the Invention

Referring now to FIG. 1, a lens 9 according to the present invention comprises a tubular body 10 which typically may be a cylinder, but the shape of which is irrelevant, which supports an entry lens 12 and an exit lens 13. The entry lens and exit lens may have the same index of refraction and may be glass. The exit lens 13 has a second convex mirror 14 disposed thereon, and the inner surface of the entry lens 12 is half silvered so as to form a first mirror 15, to collimate light reflected thereto by the second mirror 14, and direct that light through the exit lens. Within the lens system 9, a medium 18, for instance, may be water with sufficient sugar or other substance dispersed therein to match the index of refraction of the medium 18 with that of the lens 12 so that the first mirror 15 will be invisible to incoming radiation, of any sort. Also suspended within the medium 18 there are sufficient aerosol particles, such as three micron carbon particles, so as to assure a collision with a particle, which will generate a high density vapor. In FIG. 1, normal vision is provided by incident optical radiation being focused on the first mirror, reflecting from the second mirror 14 off the first mirror 15 and toward the eye or instrument, as the case may be, all as is indicated by the arrows. Aerosol induced breakdown can occur at intensity levels which are several orders of magnitude lower than the intensity level required for unassisted breakdown in air, for instance.

The breakdown phenomenon results from a free electron, accelerated by the laser radiation field, which gains sufficient energy to ionize an atom upon collision. This then becomes two electrons, and if the laser intensity is sufficiently high, leads to full ionization and, therefore, gas breakdown. The single electron energy gain process is as follows:

$$\frac{\partial E}{\partial t} = \sigma I^2 - \left(\frac{dE}{dt}\right)_l \quad \text{(EQN. 1)}$$

wherein E is the energy of an electron, $\sigma$ is the absorption cross section of the electrons, I is the laser intensity and the parenthetical is electron energy loss.

FIG. 2 illustrates that the intensity required to induce a breakdown increases significantly for pulse durations below one microsecond in air, as is described further in *Principles of Laser Plasmas*, George Bekefi, Editor: Pergamon Press, 1979; page 2300. On the other hand, the energy fluence of laser pulses of less than one microsecond, even as short as a femtosecond ($10^{-15}$ seconds), does not increase, is absorbed by the plasma, and is not transmitted beyond the breakdown. This is illustrated in FIG. 3, wherein the vertical portion 20 of the plot illustrates the point of breakdown. For short pulses (less than one microsecond) and particles of on the order of one micron diameter, the breakdown is determined by the accumulated energy fluence, that is, the integral over time of the energy per area. The unit energy fluence is, for instance, the area under the curve in FIG. 3.

The concept of the invention is to focus the incoming laser radiation with sufficient magnification to increase the laser pulse energy to a high enough level so as to generate a laser induced aerosol breakdown which will absorb 99% or more of the laser energy and thereby protect the high gain optical system (eyes or equipment) from optical damage.

To illustrate the parameters of the invention, numbers are selected from data presented in the aforementioned IEEE article. For short pulses, it is assumed that retinal damage will occur with energy levels of one joule per square centimeter. Using a mean value for the gain of an eye, for instance, of 60,000, and the incident fluence on the cornea to cause one joule per square centimeter fluence level on the retina is merely $1.6\times10^{-5}$ joules per square centimeter. This is of course, an extremely low value compared to the power levels of readily available laser sources. Utilizing previously documented data on aerosol breakdown for 10.6 micron lasers reported by Smith, David C., "Gas Breakdown Initiated by Laser Radiation Interaction with Aerosols and Solid Surfaces", J. of Applied Physics, June 1977, p. 2217, the threshold for breakdown at 1.06 micron of particles having a three-micron diameter is five joules per square centimeter. As reported in Smith, for short pulses and aerosols having three-micron diameter particles, $$J_{bd} = I_{bd} t_p = \frac{6.23}{\lambda} \text{ j/cm}^2 \quad \text{(EQN. 2)}$$

where $J_{bd}$ is the breakdown energy fluence, $I_{bd}$ is the breakdown intensity, $t_p$ is the pulse duration and $\lambda$ is the wavelength in microns. If we assume the protective measures of the invention should be effective at 0.8 micron wavelength, the invention will require a fluence of 7.78 joules per square centimeter at or near the focus.

Since the fluence of laser radiation of 0.8 micron wavelengths for pulses of less than one microsecond duration is $1.6\times10^{-5}$ joules per square centimeter, with a 5.1 centimeter diameter entry lens, the total fluence at the entry lens would be only $3.1\times10^{-4}$ joules. However, by focusing the incoming radiation, the fluence can be increased to that required for laser induced breakdown by three-micron particles, which is 7.78 joules per square centimeter. From the following, the point in the converging beam where the spot size is adequate for the breakdown threshold fluence can be determined $$\frac{3.1\times10^{-4}}{\pi/4D^2} = 7.78 \text{j/cm}^2 \quad \text{(EQN. 3)}$$

wherein D is the diameter of the spot size. Solving Equation 3, where the beam converges to a diameter of $7.1\times10^{-3}$ centimeters, the required fluence will be present. This is illustrated in FIG. 1 at the point 24. At this and all lesser diameters, the fluence is sufficient to cause radiation-absorbing breakdown, as illustrated by the stippling in FIG. 1.

Next, the particle density required for a unity probability that a three-micron particle within that focal volume will be contacted by radiation, is determined. From geometry, the volume of the plasma 25 can be determined:

$$\text{Volume} = \frac{\pi}{4}(7.1\times10^{-3})^2 9.1 \times \frac{10^{-3}}{2} = 1.8\times10^{-7} \text{ cm}^3 \quad \text{(EQN. 4)}$$

The density N, required for a unity probability of laser radiation being incident upon a three-micron particle in the volume 25, is the reciprocal of the volume thereof:

$$N = \frac{1}{1.8\times10^{-7} \text{ cm}^3} = 5.5\times10^6/\text{cm}^3 \quad \text{(EQN. 5)}$$

The absorption, $\alpha$, due to the three-micron particles in the absence of breakdown, i.e., in normal use, is:

$$\alpha=(\text{Eff.})\sigma N=(1)\{\pi/4(3\times10^{-4} \text{ cm})^2\}(5.5\times 10^{-6}/\text{cm}^3)=0.39/\text{cm} \quad \text{(EQN. 6)}$$

where Eff. is the absorption efficiency. This absorption is tolerable in the present system.

Figure 4:
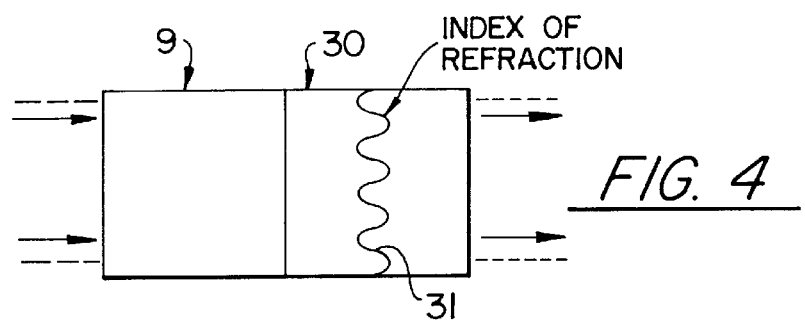

The present invention may preferably be used in an overall system which also incorporates the invention of my aforementioned application, as shown in FIG. 4. That invention provides a cell 30 with a serpentine interface 31 between media which each have an index of refraction different from the other when subjected to high intensity laser radiation, to defocus the light. In that way, protection from the first microsecond of laser radiation is provided by this invention, and protection from radiation subsequent to one microsecond, and steady state, is provided by the invention of the aforementioned application.

Figure 5:
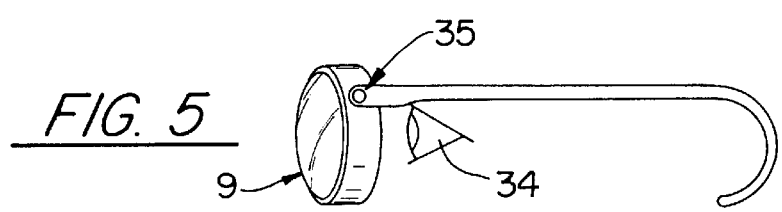

As shown in FIG. 5, eyeglasses 35 employing a cell 9 may protect an eye 34.

In the event that sufficient energy to cause breakdown does not occur prior to the occurrence of retinal damage, in accordance with the foregoing analysis, retinal damage can be prevented by putting an absorption attenuator after the device of the present invention which allows much higher energy fluence within the invention without causing sufficient energy to damage the retina. In fact, in the invention of the aforementioned application, there is a built-in, steady state attenuation of about one hundred which is provided by the density of particles required to induce thermal blooming.

Therefore, when the two are used together, it is assured that there will be adequate fluence for breakdown at a level below that which could damage the eye.

The invention is easily implemented to protect infrared devices operating in the 3 to 5 micron wavelength bands and for devices operating in the 8 to 12 micron band, which are used in cameras and detectors in a wide variety of devices and applications.

The Cassigrain-like cell 9 of FIG. 1 is of particular value where distances along the optical axis are limited and a compact laser protection device is required. On the other hand, where the distance along the optical axis is not critical, or where an optical system to be protected contains focusing optical components, either of the configurations shown in FIGS. 6 and 7 may be employed.

Figure 6:
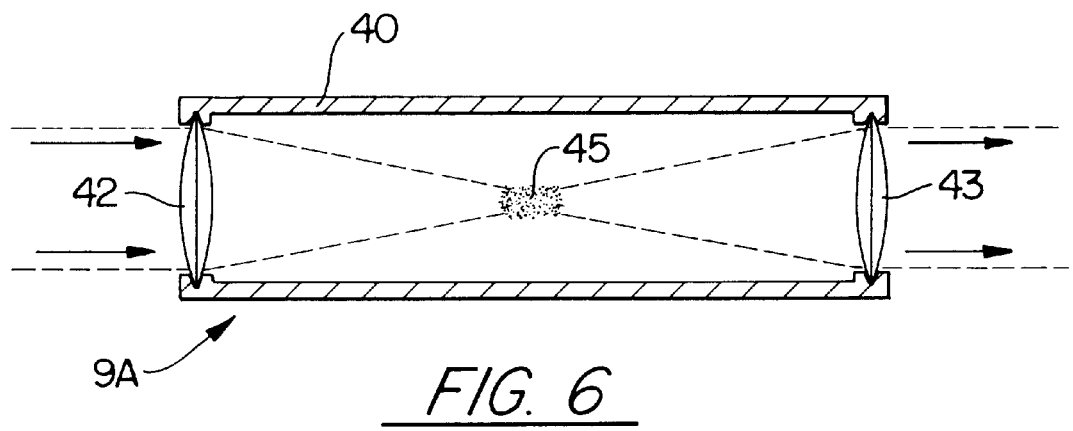

In FIG. 6, a lens 9A comprises a tubular body 40, which may typically be a cylinder, but the shape of which is irrelevant. At the entry of the cell there is a focusing lens 42 and at the exit of the cell there is a collimating lens 43. The lens 9A is filled with an aerosol ladened medium, which may be an aerosol of three micron carbon particles suspended in water, or suspended in air. The stippling shows those particles in the area 45 where the laser energy is focused sufficiently so as to induce vaporization of an aerosol particle. When the intensity is below the breakdown threshold, the optical system does not impact the transmitted beams significantly.

Figure 7:
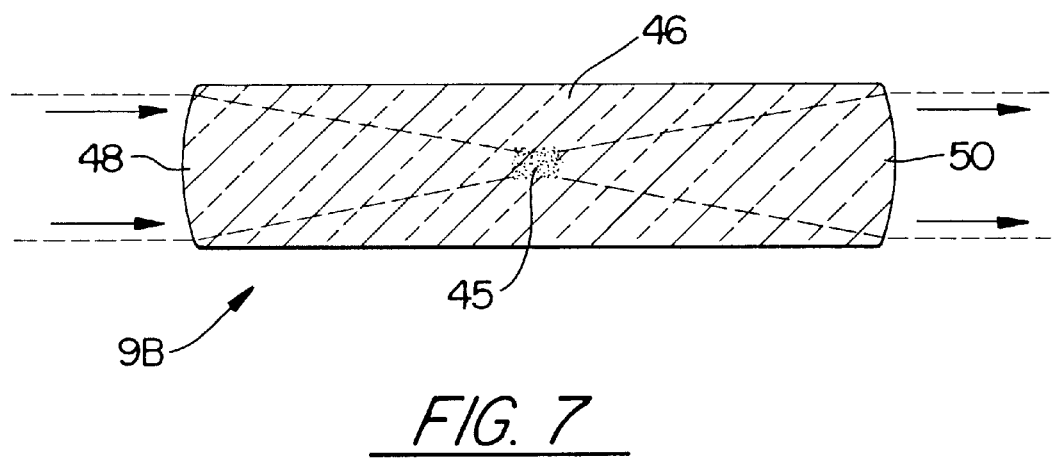

In FIG. 7, the aerosol particles, which may be carbon particles, are suspended in a solid 46, which may be a suitable lens material such as glass or polycarbonate. At the entry to the cell 9B, the solid is formed to provide a focusing surface 48, and at the exit of the cell 9B, the solid is formed to form a collimating surface 50. The apparatus of FIG. 7 can only be used one time to protect an optical system since the process is irreversible because a breakdown induced in the solid produces permanent damage to the solid that exceeds the size of the aerosol by many orders of magnitude. On the other hand, the solid would have a longer shelf life than the water or air suspension of FIGS. 1 or 6, and it will be inexpensive End rugged.

The aforementioned patent is incorporated herein by reference.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A lens system for protecting high gain optical systems from damage due to high intensity laser radiation, comprising:

a tubular case;

an exit lens disposed in a first end of said tubular case;

an entry lens disposed in a second end of said case opposite to said first end, said case, said entry lens and said exit lens forming a closed volume, an external surface of said entry lens having a convex radius of curvature so as to focus incoming radiation onto a spot, an internal surface of said entry lens having a half-silvered concave radius of curvature forming a first mirror which collimates radiation directed thereto from said spot and directs said collimated radiation through said exit lens;

a convex second mirror disposed at said spot; and a medium disposed in said closed volume having an index of refraction substantially the same as that of said entry lens and containing aerosol particles, whereby laser radiation is focused in said volume to vaporize at least some of said particles.

2. A system according to claim 1 wherein said exit lens and said entry lens have the same index of refraction.

3. A system according to claim 2 wherein said exit lens and said entry lens are glass.

4. A system according to claim 1 wherein said second mirror is disposed on said exit lens.

5. A system according to claim 1 wherein said tubular case is cylindrical.

6. A system according to claim 1 wherein said medium includes water.

7. A system according to claim 1 wherein said medium includes aerosol particles of about three microns in diameter.

8. A system according to claim 1 wherein said medium includes carbon particles.

9. A system according to claim 8 wherein said carbon particles are of about three microns in diameter.

10. A system according to claim 1 wherein said particles have a number density of about $5.5 \times 10^6$ particles per cubic centimeter.

11. A system according to claim 1 wherein said entry lens has a round perimeter.

12. A system according to claim 1 further comprising:
means, disposed to receive said collimated radiation from said exit lens, and including a second medium, said second medium having, when irradiated by high intensity laser radiation, an index of refraction which varies spatially periodically along one dimension perpendicular to said collimated radiation, thereby to induce a spatially varying phase change in said radiation, whereby said radiation will be significantly defocused along said one dimension.

13. A system according to claim 1 wherein said high gain optical system is a human eye and said lens system is part of a pair of protective eyeglasses.

14. A method for protecting an optical system from damage due to high intensity laser radiation, comprising:
providing a focusing means;
using said focusing means to focus laser radiation aimed at said optical system into a medium having an index of refraction substantially the same as said focusing means and having a sufficient density of particles suspended therein to assure illumination of said particles by said radiation at a sufficiently high energy fluence to vaporize said particles and ionize the resulting vapor, which absorbs said laser radiation.

15. A lens system for protecting high gain optical systems from damage due to high intensity laser radiation, comprising:
a tubular case;
a collimating exit lens disposed in a first end of said tubular case;
a focusing entry lens disposed in a second end of said case opposite to said first end, said case, said entry lens and said exit lens forming a closed volume, said entry lens focusing incoming radiation onto a spot, radiation directed through said spot being collimated through said exit lens; and
a medium disposed in said closed volume having is an index of refraction substantially the same as that of said entry lens and containing aerosol particles, whereby laser radiation focused at said spot vaporizes at least some of said particles.

16. A system according to claim 15 wherein said tubular case is cylindrical.

17. A system according to claim 15 wherein said medium includes water.

18. A system according to claim 15 wherein said medium includes air.

19. A system according to claim 15 wherein said medium includes aerosol particles of about three microns in diameter.

20. A system according to claim 15 wherein said medium includes carbon particles.

21. A system according to claim 15 further comprising:
means, disposed to receive said collimated radiation from said exit lens, and including a second medium, said second medium having, when irradiated by high intensity laser radiation, an index of refraction which varies spatially periodically along one dimension perpendicular to said collimated radiation, thereby to induce a spatially varying phase change in said radiation, whereby said radiation will be significantly defocused along said one dimension.

22. A system according to claim 15 wherein said high gain optical system is a human eye and said lens system is part of a pair of protective eyeglasses.

23. A system according to claim 15 wherein said tubular case is cylindrical.

24. A lens system for protecting high gain optical systems from damage due to high intensity laser radiation, comprising:
a structure formed of lens material;
a collimating exit lens formed in a first end of said structure;
a focusing entry lens formed in a second end of said structure opposite to said first end, said entry lens focusing incoming radiation onto a spot, radiation directed through said spot being collimated through said exit lens; and
said lens material ladened with aerosol particles, whereby laser radiation focused at said spot vaporizes at least some of said particles.

25. A system according to claim 24 wherein said lens material includes glass.

26. A system according to claim 24 wherein said lens material includes polycarbonate.

27. A system according to claim 24 wherein said lens material includes carbon particles.

28. A system according to claim 24 further comprising:
means, disposed to receive said collimated radiation from said exit lens, and including a second medium, said second medium having, when irradiated by high intensity laser radiation, an index of refraction which varies spatially periodically along one dimension perpendicular to said collimated radiation, thereby to induce a spatially varying phase change in said radiation, whereby said radiation will be significantly defocused along said one dimension.

29. A system according to claim 24 wherein said high gain optical system is a human eye and said lens system is part of a pair of protective eyeglasses.

* * * * *